(12) United States Patent
Zavislan et al.

(10) Patent No.: US 7,813,788 B2
(45) Date of Patent: Oct. 12, 2010

(54) MICROSCOPIC IMAGING APPARATUS AND METHOD

(75) Inventors: James M. Zavislan, Pittsford, NY (US); Jay M. Eastman, Pittsford, NY (US)

(73) Assignee: Lucid, Inc., Rochester, NY (US)

( * ) Notice: Subject to any disclaimer, the term of this patent is extended or adjusted under 35 U.S.C. 154(b) by 1085 days.

(21) Appl. No.: 11/013,099

(22) Filed: Dec. 15, 2004

(65) Prior Publication Data

US 2005/0101871 A1      May 12, 2005

Related U.S. Application Data

(63) Continuation of application No. 09/579,599, filed on May 26, 2000, now Pat. No. 7,047,064, which is a continuation of application No. 09/001,016, filed on Dec. 30, 1997, now Pat. No. 6,263,233, which is a continuation of application No. 08/650,684, filed on May 20, 1996, now Pat. No. 5,788,639.

(60) Provisional application No. 60/001,141, filed on Jul. 13, 1995.

(51) Int. Cl.
    *A61B 6/00*      (2006.01)
(52) U.S. Cl. .......................... 600/476; 606/10
(58) Field of Classification Search ............... 606/8–12; 607/88–92; 60/476; 128/898
    See application file for complete search history.

(56) References Cited

U.S. PATENT DOCUMENTS

| 4,768,874 A | 9/1988 | Webb |
| 4,817,622 A | 4/1989 | Pennypacker |
| 4,863,252 A | 9/1989 | McCarthy et al. |
| 4,965,441 A | 10/1990 | Picard |
| 4,991,953 A | 2/1991 | Pflibsen |
| 5,048,904 A | 9/1991 | Montagu |
| 5,048,942 A | 9/1991 | Ohbayashi |
| 5,120,953 A * | 6/1992 | Harris ..................... 250/227.2 |
| 5,122,653 A | 6/1992 | Ohki |
| 5,321,683 A | 6/1994 | Olczak |
| 5,386,317 A | 1/1995 | Corle et al. |
| 5,464,436 A | 11/1995 | Smith |

(Continued)

FOREIGN PATENT DOCUMENTS

DE      32 31 483 A1      3/1984

(Continued)

OTHER PUBLICATIONS

Delaney, P. et al., Fibre optic confocal imaging (FOCI) for subsurface microscopy of the colon in vivo, J. Anat. 184, 157-160 (1994).

(Continued)

*Primary Examiner*—Ahmed M Farah
(74) *Attorney, Agent, or Firm*—Kenneth J. Lukacher

(57) ABSTRACT

A handheld confocal imaging system for in vivo observation of dermal and subdermal tissue allows diagnosis of conditions substantially beneath the surface of the skin. A confocal head has optics which scan the tissue so as to provide images of vertical sections of the tissue. Both two and three dimensional imaging may be provided for diagnosis and location of basal cell carcinomas and melanomas, and so as to enable visualization of tumor borders prior to excision.

35 Claims, 2 Drawing Sheets

U.S. PATENT DOCUMENTS

| | | | |
|---|---|---|---|
| 5,532,874 | A | 7/1996 | Stein |
| 5,557,452 | A | 9/1996 | Harris |
| 5,687,251 | A * | 11/1997 | Erler et al. .................. 382/133 |
| 5,699,798 | A | 12/1997 | Hochman et al. |
| 5,719,700 | A * | 2/1998 | Corcuff et al. .............. 359/368 |
| 5,725,522 | A * | 3/1998 | Sinofsky ........................ 606/8 |
| 5,788,639 | A * | 8/1998 | Zavislan et al. ............. 600/476 |
| 5,880,880 | A | 3/1999 | Anderson et al. |
| 5,995,283 | A | 11/1999 | Anderson et al. |
| 6,032,071 | A * | 2/2000 | Binder ....................... 600/476 |
| 6,263,233 | B1 * | 7/2001 | Zavislan et al. ............. 600/476 |
| 6,706,035 | B2 * | 3/2004 | Cense et al. ................... 606/9 |
| 7,047,064 | B1 * | 5/2006 | Zavislan et al. ............. 600/476 |

FOREIGN PATENT DOCUMENTS

| | | |
|---|---|---|
| EP | 0 683 386 A1 | 5/1995 |
| JP | 8-140961 | 6/1994 |
| WO | WO 92/17806 | 10/1992 |
| WO | WO92/19930 | 11/1992 |
| WO | WO96/21938 | 7/1996 |

OTHER PUBLICATIONS

Delaney, P. et al., Novel Microscopy Using Fibre Optic Confocal Imaging and its Suitability for Subsurface Blood Vessel Imaging in Vivo, Clinical and Experimental Pharmacology and Physiology, 20, 197-198 (1993).

Rajadhyakasha et al., "In Vivo Confocal Scanning Laser Microscopy of Human Skin: Melanin Provides Strong Contrast", The Journal of Investigative Dermatology vol. 104, No. 6. Jun. 1997.

Brumberg et al., "Hand-held contact microscope for medical examinations", Soviet Journal of Optical Technology, Jan. 1974, vol. 41, No. 1.

Small Business Innovation Research Prog; Issued Sep. 28, 1992; Grant No. SSS-3 (BA) 1 R43 RRo7737-01; awarded by National Center for Research Resources; entitled Confocal Laser Scanning Microscope- Video, Vector & Zoom.

Delaney, P. et al., Fiber-optic laser scanning confocal microscope suitable for fluorescence imaging, Applied Optics, vol. 33, No. 4, pp. 573-577 (1994).

Maurice, D. Cellular Membrane Activity in the Cornear Endothelium of the Intact Eye, Experientia, vol. 24, pp. 1094-1095, (1968).

Maurice, D., A Scanning Slit Optical Microscope, Investigative Ophthalmology, vol. 13, No. 12, pp. 1033-1037, (1974).

Koester, C., Scanning Mirror Microscope With Optical Sectioning Characteristics: Applications in Ophthalmology, Applied Optics, vol. 19, No. 11, pp. 1749-1757, Jun. 1980.

New, K.C., et al., In Vivo Imaging of Human Teeth and Skin Using Real-Time Confocal Microscopy, Scanning, vol. 13, 369-372 (1991).

Corcuff, P. et al., Morphometry of Human Epidermis In Vivo by Real-time Confocal microscopy, Arch Dermatol Res 285:475-481 (1993).

* cited by examiner

MICROSCOPIC IMAGING APPARATUS AND METHOD

This application is a continuation of application Ser. No. 09/579,599, filed May 26, 2000, now U.S. Pat. No. 7,047,064, which is a continuation of application Ser. No. 09/001,016, filed Dec. 30, 1997, now U.S. Pat. No. 6,263,233, which is a continuation of application Ser. No. 08/650,684 filed May 20, 1996, now U.S. Pat. No. 5,788,639, which claims the priority benefit of provisional application, Ser. No. 60/001,141, filed Jul. 13, 1995.

FIELD OF THE INVENTION

The present invention relates to handheld confocal imaging system for in vivo clinical examinations of dermal and subdermal tissues using non-ionizing radiation, and particularly laser radiation which is of a wavelength capable of penetrating into the skin.

The invention is especially suitable for providing an instrument for dermal pathology applications. The invention is also applicable for visualizing sections in other scattering media than tissue. The invention enables the use of a laser as a source of illumination. The instrument may provide data to image processing computers, which may be programmed to provide high resolution images of dermal sections.

BACKGROUND OF THE INVENTION

Systems have been proposed for viewing the surface areas of the skin or the external surfaces of internal tissue. Viewing without scanning is described in Pennypacker, U.S. Pat. No. 4,817,622, issued Apr. 4, 1989. Examination of internal tissue surfaces by means of beam scanning are proposed in Harris, U.S. Pat. No. 5,120,953, issued Jun. 9, 1992, Ohki, U.S. Pat. No. 5,122,653 issued Jun. 16, 1992, Webb, U.S. Pat. No. 4,768,874 issued Sep. 6, 1988 and Pflibsen, U.S. Pat. No. 4,991,953 issued Feb. 12, 1991. Such proposals have not provided a handheld instrument which is readily usable by a surgeon in clinical examinations for imaging the epidermis and dermis, especially in vertical sections or in horizontal sections at desired depths below the surface of the skin.

SUMMARY OF THE INVENTION

Accordingly, it is the principal object of the present invention to provide and improve clinical dermatological imaging system.

It is another object of the invention to provide an improved confocal imaging system which provides images of dermatological tissues and avoids the need for biopsies to detect the location of such abnormalities as basal cell carcinomas and melanomas.

It is a still further object of the present invention to provide an improved confocal dermatological imaging system which does not require ionizing radiation and may use a laser beam.

It is a still further object of the present invention to provide an improved confocal imaging system which provides in vivo imaging of dermatological tissue both at and below the skin and which may be handheld and which is capable of operating in various scattering media.

It is a still further object of the present invention to provide an improved confocal dermatological imaging system which may use a computer to generate images from data produced by the optics which provides confocal imaging and to display or provide images for further evaluation or computer enhancement.

BRIEF DESCRIPTION OF THE DRAWINGS

The foregoing objects, features and advantages of the invention will become more apparent from a reading of the following description in connection with the accompanying drawings in which.

DETAILED DESCRIPTION OF THE INVENTION

Figure 1:
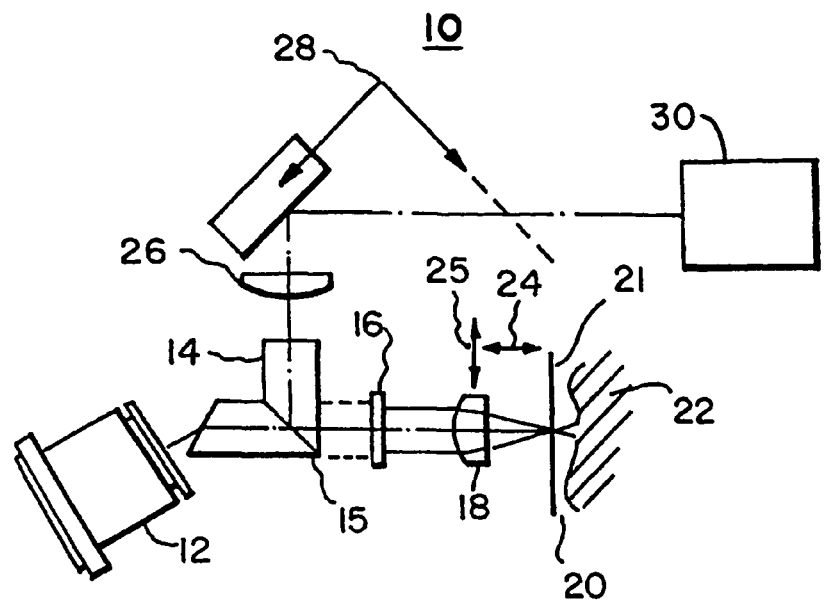
FIG. 1 is schematic diagram of a confocal imaging system embodying the invention.
Figure 1A:
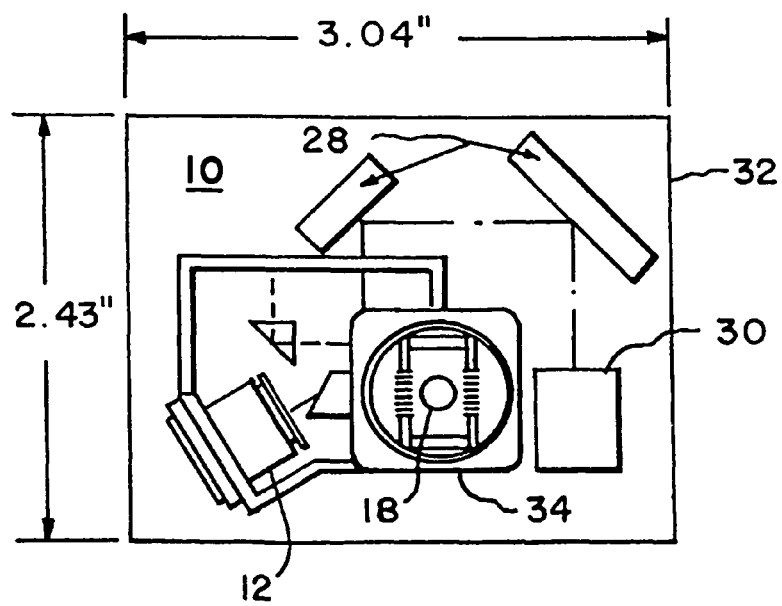
FIG. 1a is a plan view of the head of the system shown in FIG. 1.

Referring to FIG. 1 there is shown a system 10 for in vivo diagnosis of dermatological tissues. The system 10 may be embodied in a handheld head 32 as shown in FIG. 1a and schematically in FIG. 3.

Referring more particularly to FIG. 1 there is shown a system 10 (or instrument) which contains optics of the type which are used in optical data storage heads which are used in recording and reading optical disks. Light from a laser diode, contained in a laser and collimator assembly 12, is collimated by a diffraction limited lens in the assembly 12 and is incident at an oblique angle on a beam splitter assembly 14. Refraction at this oblique angle causes the elliptical laser diode beam to become circular in cross-section. The circular beam passes through the beam splitter assembly 14 and a quarter wave plate 16 and is focused into the tissue 22 via a contact window 20 (a glass window plate) spaced from the sample, specimen or tissue 22 being examined, preferably by an optical contact liquid 21. In the event the sample is viscus or liquid, it may be located in a sample well (not shown).

The circular beam which passes through the beam splitter assembly 14 and the quarter wave plate 16 is focused into the sample by a precision focusing lens 18, which suitably has a numerical aperture of 0.5 and a focal length of 4.3 millimeters. These dimensions and parameters are exemplary and demonstrate that the optical system 10 may be miniaturized so as to be adapted to be handheld.

The quarter wave plate 16 converts the incident linear polarization from the laser in assembly 12 to circular polarization, i.e., the quarter wave plate is oriented 45° to the incident polarization. In other words, the beam from plate 16 is circularly polarized. The focusing lens 18 is movable both in a direction along its optical axis and laterally as indicated by the arrows 24 and 25, respectively. Position mechanical actuators 34 (FIG. 1a) may be used for moving the lens 18, and thereby control position of the focus spot of beam in the sample. These actuators 34 may be similar to those used in optical disk systems. The lens 18 may be mounted on a pair of such mechanical actuators. The actuators 34 provide lateral and vertical scanning of the focused laser beam in the tissue sample.

The focusing lens 18 also collects scattered light reflected from the sample. The amount of coherent light scattered back into the detection system (which includes lens 18, plate 16 and assembly 14) depends upon local variations of the refractive index and the absorption in the immediate neighborhood of the focus spot. This coherent light may be defined as the component of the reflected light having a circular polarization orthogonal to the polarization of the beam focused into the tissue sample. The scattered light is incident to plate 16 and then to beam splitter assembly 14. The plate 16 converts the coherent component of the scattered light into linear polarization, where beam splitter assembly 14 directs by reflection (or filters) the coherent light component of the scattered light at the beam splitting surface 15 in the beam splitter assembly 14. The reflected light passes through a relay lens 26. The light from relay lens 26 may be reflected from a pair of fold mirrors 28 (See also FIG. 1a). These fold mirrors 28 may be part of the beam splitter assembly 14. The relay lens 26 may also be part of this assembly 14.

The scanned light from the focus spot is reflected from the fold mirrors 28 to a pinhole photodetector assembly 30, which may also be considered part of the detection system. The fold mirrors 28 are used to make the instrument more compact. A prism assembly may alternatively be used, which is part of the beam splitting assembly 14, and allows the samples to be placed face down. This orientation allows gravity to assist in maintaining the sample in a stable viewing position. Maintaining a stable viewing position is also enhanced by the use of the window 20 as shown in FIG. 1.

A top view of the instrument is illustrated in FIG. 1a. Typical dimensions are given in FIG. 1a to illustrate the compacted size of the confocal imaging head 32. The elements in the head 32 may be located on a single board to provide unitized construction. The height of the head may be approximately two inches from the base to the nominal focal point of the focusing lens 18.

By scanning using the mechanical actuators 34 successive lines may be scanned at successive depths to provide images of vertical sections (i.e., along a vertical plane through the tissue sample). If desired the images may be formed from horizontal sections (i.e., along a horizontal plane through the tissue sample) as the lines are scanned horizontally. By tilting the sample, sections at desired angles to the surface of the sample (i.e., along a tilted or non-perpendicular plane) may be formed, such sections may also be formed by moving the lens 18 via actuator 34 as desired angles.

Figure 2:
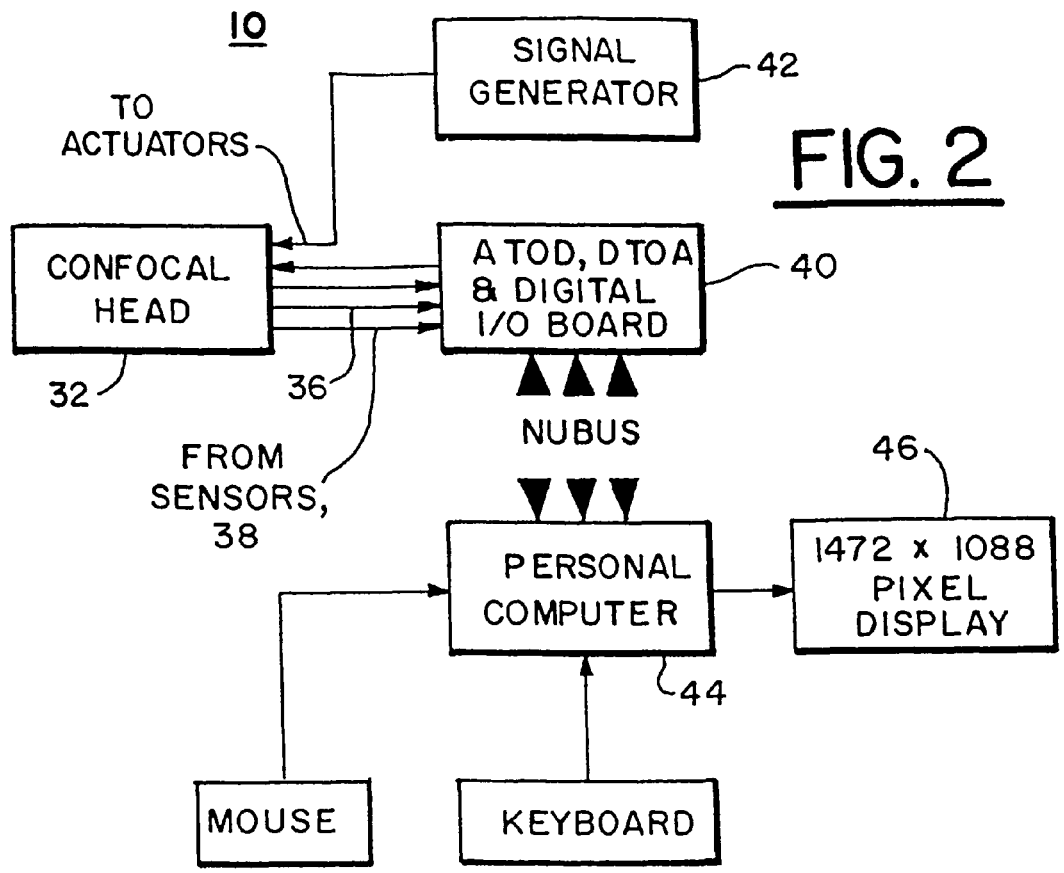
FIG. 2 is a block diagram of the system shown in FIG. 1, and especially the computer control and imaging system for acquisition and processing of the optical image.

Referring to FIG. 2, there is shown a block diagram of the data acquisition and analysis system which is part of the imaging system 10 provided by the invention. The confocal head 32 is the head shown in FIGS. 1 and 1a. The output 36 from the head 32 is the output from the pinhole detector assembly 30. This output 36 is the confocal detector signal. Signals are also provided from sensors 38, namely a lateral position sensor and a vertical position sensor. These signals after amplification and filtering are acquired by a analog to digital converter of a digital I/O board 40. This board 40 may also be on a board with a circuit which provides a digital to analog channel to drive the lateral motion actuator. The vertical scanning actuator is driven from a signal derived from a conventional signal generator 42. The A to D, D to A and digital I/O board 40 is controlled and data is acquired via software in a personal computer 44, such as a Macintosh Quadra 950. Conventional software packages may be used for image analysis and for driving a display 46, which is shown by way of example as a 1472 by 1088 pixel display.

Figure 3:
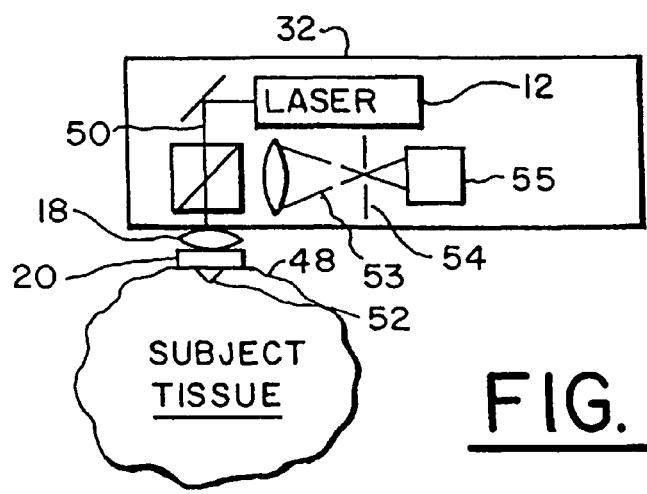
FIG. 3 is a schematic diagram of the handheld confocal imaging system of FIG. 2 in use.

Referring to FIG. 3, there is shown the confocal imaging head 32 contacted against the skin 48 of a subject specimen using a mineral oil as an optical index matching fluid, which is an optical contact liquid 21 (FIG. 1) for reducing undesired reflections of light from the surface of the skin. The force against the skin 48 will be limited to that required to press the skin against the contact window 20 of the head 32. A laser beam 50 which may be relatively low power (e.g., 6.3 milliwatts of optical power) is focused into the dermis of the specimen. The laser is operated at a wavelength capable of penetrating into the skin of the specimen, thus the skin may be considered transparent to the laser wavelength (or in other words, the skin is permeable to electromagnetic radiation of specified frequencies). The depth of focal point or spot 52 is varied from the surface of the stratum corneum to a few millimeters below the surface of stratum corneum. The nominal beam spot size may be, for example, 2.5 micrometers, full width half maximum. The laser spot is scanned laterally across the skin, for example at a rate of 3 to 10 hz. Different laser wavelengths may be selectively used for different resolution. Inasmuch as the energy delivered is proportional to the illuminating flux focused divided by the diameter of the spot, the scan length and the scan rate or frequency, the amount of incident flux is sufficiently low that damage to the specimen is avoided. The light scattered by the tissue is collected and the lights coherent component is re-imaged onto the pinhole aperture 54 of assembly 30, as shown in FIGS. 1 and 1a. The pinhole 54 transmits the coherent light from the focal region of the incident beam 53 to the detector 55 (of assembly 30) where it converts the light into an electrical signal. As the lens 18 scans laterally, the electrical signal is acquired by the computer and stored. Each scan represents a one dimensional trace of the reflectivity and scattering cross section of the dermis at a given level below the surface of the skin 48. A series of scans are made with the focal point positioned at progressively lower depths thereby providing a vertical cross section image of the skin which may be similar to a B-scan ultrasound image. As stated earlier, these scans may also be horizontal to provide a horizontal cross-section, or at an angle to provide an angular cross-section of the skin.

From the foregoing description it will be apparent that there has been provided an embodiment of a confocal imaging system for dermatological pathology applications. Variations and modifications of the herein described system and other applications for the invention will undoubtedly suggest themselves to those skilled in the art. Accordingly, the foregoing description should be taken as illustrative and not in a limiting sense.

What is claimed is:

1. A microscopic imaging apparatus for imaging tissue for pathological applications through an objective lens, said apparatus comprising:
    an objective lens;
    a window having a surface capable of being pressed into a contact relationship with the surface of said tissue in which said window is in optical communication with said objective lens;
    a medium between said window and the surface of said tissue in which said contact relationship between said window and the surface of said tissue is provided using said medium;
    a housing capable of being handheld having at least said objective lens and said window; and
    an illumination beam which is focused by said objective lens through said surface of said window to said tissue, wherein said objective lens receives returned light from said tissue representing a tissue section, wherein said medium reduces reflections from the surface of said tissue when illuminated by said beam.

2. The apparatus according to claim 1 further comprising a light source for said illumination beam.

3. The apparatus according to claim 1 wherein said objective lens has a numerical aperture of less than one.

4. The apparatus according to claim 1 wherein said housing is positionable to locate said window in direct contact with said surface of said tissue using said medium.

5. The apparatus according to claim 1 further comprising means in said housing for detecting the returned light received by said objective lens to provide electrical signals representative of said tissue section.

6. The apparatus according to claim 1 wherein said illumination beam is focused by said objective lens to a variable depth from the surface of the tissue to a depth below the surface of the tissue.

7. The apparatus according to claim 6 wherein said illumination beam is of a wavelength adapted to penetrate the tissue when one of dermal or subdermal tissue.

8. The apparatus according to claim 1 wherein the surface of said tissue and said window are in said contact relationship using said medium when said illumination beam is focused by said objective lens through said window to said tissue and said objective lens receives returned light from said tissue representing said tissue section.

9. The apparatus according to claim 1 wherein said medium is a liquid.

10. The apparatus according to claim 1 wherein said medium is of an optical index for reducing said reflections from the surface of said tissue.

11. The apparatus according to claim 1 wherein said medium is an optical index matching fluid.

12. A microscopic imaging apparatus for imaging tissue for pathological applications through an objective lens, said apparatus comprising:
an objective lens;
a window having a surface capable of being pressed into a contact relationship with the surface of said tissue in which said window is in optical communication with said objective lens;
an illumination beam which when focused by said objective lens through said surface of said window to said tissue said objective lens receives returned light;
a detector and an aperture, in which said detector receives said returned light, via said aperture, to provide an electrical signal output representing a tissue section; and
a housing capable of being handheld having at least said objective lens, said window, said detector, and said aperture, in which at least said electrical signal output is outputted from said housing.

13. The apparatus according to claim 1 wherein said illumination beam is focused by said objective lens through said window to locations on or within said tissue in accordance with said tissue section.

14. The apparatus according to claim 1 wherein said section represents one of a horizontal, vertical, or angled section on or within said tissue.

15. The apparatus according to claim 12 wherein said objective lens has a numerical aperture of less than one.

16. A microscopic imaging apparatus for imaging one or more tissue samples for pathological applications through an objective lens, said apparatus comprising;
an objective lens;
a window having a surface that is capable being in a direct pressure contacting relationship with the surface of said tissue sample;
a housing capable of being handheld having at least said window in optical communication with said objective lens; and
an illumination beam which is focused by said objective lens through said surface of said window to said tissue sample when said window and said tissue sample are in said pressure contacting relationship, and said objective lens receives returned light from said tissue sample representing a tissue section within or on the illuminated tissue sample; and a detector for receiving the returned light from said objective lens that represents said tissue section and converting said returned light received into an electrical signal output representing said tissue section, and said housing further comprises said detector.

17. The apparatus according to claim 16 wherein said section is capable of being formed by said returned light along a region of said focused illumination beam under the surface of said tissue.

18. The apparatus according to claim 16 further comprising a light source for said illumination beam.

19. The apparatus according to claim 16 wherein said objective lens has a numerical aperture of less than one.

20. The apparatus according to claim 16 wherein said housing is positionable to locate said window in direct contact with said surface of said tissue sample.

21. The apparatus according to claim 16 wherein said section represents one of a horizontal, vertical, or angled section on or within said tissue.

22. The apparatus according to claim 16 wherein said pressure contacting relationship with the surface of said tissue is enabled solely by direct contact pressure.

23. The apparatus according to claim 16 wherein at least said electrical signal output is outputted from said housing.

24. A method for diagnosing a tumor in images of one or more sections of in-vivo tissue comprising the steps of:
placing said in-vivo tissue against a window having a surface in a pressure contact relationship with the surface of said tissue;
locating a medium on said tissue facing said window when said window is placed in said pressure contact relationship with said tissue;
imaging the tissue through an objective lens and said surface of said window to provide at least one image of a section of the tissue while said placing step is being carried out, in which said medium reduces imaging of reflections from the surface of said tissue; and
diagnosing in said image one or more cells of a tumor in said tissue.

25. The method according to claim 24 further comprising the step of focusing an illumination beam with said objective lens through said window to said tissue sample.

26. The method according to claim 25 further comprising the step of providing a light source for said illumination beam.

27. The method according to claim 24 wherein said tumor represents one of carcinomas and melanomas.

28. The method according to claim 24 wherein said placing step further comprises the step of pressing said surface of said window into said pressure contact relationship with said surface of said tissue.

29. The method according to claim 24 further comprising the step of visualizing the borders of the tumor in said image.

30. The method according to claim 29 further comprising the step of excising the tumor cells from said tissue.

31. The method according to claim 24 wherein the pressure contact relationship between said surface of said window and the surface of said tissue is provided solely by direct contact pressure.

32. The method according to claim 24 wherein said located medium is a liquid.

33. A method for diagnosing a tumor in images of one or more sections of in-vivo tissue comprising the steps of:
placing said in-vivo tissue against a window having a surface in a pressure contact relationship with the surface of said tissue;

imaging the tissue through an objective lens and said surface of said window to provide at least one image of a section of the tissue while said placing step is being carried out;

diagnosing in said image one or more cells of a tumor in said tissue, wherein said imaging step comprises the steps of:

receiving return light from said tissue;

converting the returned light into electrical signals; and processing said electrical signals to provide an image of said tissue section; and providing a housing capable of being handheld having at least said window and said objective lens, in which at least said receiving and said converting steps are carried out in said housing.

34. The method according to claim 33 wherein said imaging step further comprising the step of outputting said electrical signals from said housing in which said processing step is carried out outside of said housing.

35. The method according to claim 34 wherein said processing step is carried out with the aid of a computer system.

* * * * *